US 7,674,228 B2

(12) United States Patent
Williams et al.

(10) Patent No.: US 7,674,228 B2
(45) Date of Patent: Mar. 9, 2010

(54) SYSTEM AND METHOD FOR ECG-TRIGGERED RETROSPECTIVE COLOR FLOW ULTRASOUND IMAGING

(75) Inventors: Ross Williams, Toronto (CA); Andrew Needles, Toronto (CA); Emmanuel Cherin, Ontario (CA); F. Stuart Foster, Toronto (CA)

(73) Assignee: Sunnybrook and Women's College Health Sciences Centre, Toronto (CA)

( * ) Notice: Subject to any disclaimer, the term of this patent is extended or adjusted under 35 U.S.C. 154(b) by 714 days.

(21) Appl. No.: 11/068,565

(22) Filed: Feb. 28, 2005

(65) Prior Publication Data

US 2005/0197572 A1    Sep. 8, 2005

Related U.S. Application Data

(60) Provisional application No. 60/549,041, filed on Mar. 1, 2004.

(51) Int. Cl.
*A61B 8/00* (2006.01)
*G06K 9/00* (2006.01)

(52) U.S. Cl. .................. 600/437; 600/441; 382/162
(58) Field of Classification Search ............ 600/437, 600/441, 447; 382/128, 162, 254
See application file for complete search history.

(56) References Cited

U.S. PATENT DOCUMENTS

| | | |
|---|---|---|
| 3,974,826 A | 8/1976 | Eggleton et al. |
| 4,034,744 A | 7/1977 | Goldberg |
| 4,141,347 A | 2/1979 | Green et al. |
| 4,412,147 A | 10/1983 | Nagura et al. |
| 4,413,521 A | 11/1983 | Van Kemenade |
| 4,431,007 A | 2/1984 | Amazeen et al. |
| 4,489,729 A | 12/1984 | Sorenson et al. |
| 4,546,771 A | 10/1985 | Eggleton et al. |
| 4,612,937 A | 9/1986 | Miller |
| 4,664,123 A | 5/1987 | Iinuma |
| 4,722,346 A | 2/1988 | Chen |

(Continued)

FOREIGN PATENT DOCUMENTS

WO    WO 98/40014    9/1998

(Continued)

OTHER PUBLICATIONS

Berson et al., "High Frequency Unltrsonic Devices: Advantages and Applications." European Journal of Ultrasound; vol. 10:53-63, (1999).

(Continued)

*Primary Examiner*—Eric F Winakur
*Assistant Examiner*—Katherine L Fernandez
(74) *Attorney, Agent, or Firm*—Kristina Bieker-Brady; Clark & Elbing LLP

(57) ABSTRACT

A method for producing an ECG-triggered retrospective color-flow ultrasound image comprises generating ultrasound, transmitting the ultrasound into a subject at a first location, wherein a first reference point of an ECG signal taken from the subject triggers the ultrasound transmission, receiving ultrasound reflected from the subject at the first location, transmitting the ultrasound into the subject at a second location, wherein a second reference point of an ECG signal taken from the subject triggers the ultrasound transmission receiving ultrasound reflected from the subject at the second location, processing the received ultrasound to form ultrasound color traces, and reconstructing the ultrasound color traces to form the ultrasound image.

15 Claims, 10 Drawing Sheets

U.S. PATENT DOCUMENTS

| | | | |
|---|---|---|---|
| 4,790,321 A | 12/1988 | Miwa et al. ............ | 128/660.07 |
| 4,796,632 A | 1/1989 | Boyd | |
| 4,867,169 A | 9/1989 | Machida et al. | |
| 4,888,694 A | 12/1989 | Chesarek | |
| 4,991,589 A | 2/1991 | Hongo et al. | |
| 5,099,847 A | 3/1992 | Powers et al. | |
| 5,105,814 A | 4/1992 | Drukarey et al. | |
| 5,119,342 A | 6/1992 | Harrison, Jr. et al. | |
| 5,161,536 A | 11/1992 | Vilkomerson et al. | |
| 5,165,413 A * | 11/1992 | Maslak et al. ............... | 600/441 |
| 5,192,549 A | 3/1993 | Barenoiz et al. | |
| 5,278,757 A | 1/1994 | Hoctor et al. | |
| 5,313,949 A | 5/1994 | Yock | |
| 5,313,950 A | 5/1994 | Ishikawa et al. | |
| 5,379,642 A | 1/1995 | Reckwerdt et al. | |
| 5,390,674 A | 2/1995 | Robinson et al. | |
| 5,474,074 A | 12/1995 | Suorsa et al. | |
| 5,485,845 A | 1/1996 | Verdonk et al. | |
| 5,488,954 A | 2/1996 | Sleva et al. | |
| 5,513,640 A | 5/1996 | Yamazaki et al. | |
| 5,524,623 A | 6/1996 | Liu | |
| 5,579,771 A | 12/1996 | Bonnefous | |
| 5,588,434 A | 12/1996 | Fujimoto | |
| 5,588,435 A | 12/1996 | Weng et al. | |
| 5,615,680 A | 4/1997 | Sano | |
| 5,651,366 A | 7/1997 | Liang et al. | |
| 5,655,537 A | 8/1997 | Crowley | |
| 5,690,110 A | 11/1997 | Tanaka | |
| 5,709,210 A * | 1/1998 | Green et al. ............... | 600/453 |
| 5,724,312 A | 3/1998 | Oppelt | |
| 5,776,068 A | 7/1998 | Silverman et al. | |
| 5,792,058 A | 8/1998 | Lee et al. | |
| 5,797,846 A | 8/1998 | Seyed-Bolorforosh et al. | |
| 5,839,442 A | 11/1998 | Chiang et al. | |
| 5,844,140 A | 12/1998 | Seale | |
| 5,865,650 A | 2/1999 | Marian, Jr. et al. | |
| 5,879,305 A | 3/1999 | Yock et al. | |
| 5,921,931 A | 7/1999 | O'Donnell et al. | |
| 5,940,123 A | 8/1999 | Daigle et al. | |
| 6,036,647 A | 3/2000 | Suorsa et al. | |
| 6,042,545 A | 3/2000 | Hossack et al. | |
| 6,055,861 A | 5/2000 | Banta, Jr. et al. | |
| 6,063,030 A | 5/2000 | Vara et al. | |
| 6,066,099 A | 5/2000 | Thomenius et al. | |
| 6,099,473 A | 8/2000 | Liu et al. | |
| 6,123,670 A | 9/2000 | Mo et al. | |
| 6,139,500 A | 10/2000 | Clark | |
| 6,139,502 A | 10/2000 | Fredrikson | |
| 6,152,877 A | 11/2000 | Masters | |
| 6,193,662 B1 | 2/2001 | Hwang | |
| 6,193,664 B1 * | 2/2001 | Guracar et al. ............... | 600/453 |
| 6,200,267 B1 | 3/2001 | Burke | |
| 6,201,900 B1 | 3/2001 | Hossack et al. | |
| 6,221,016 B1 | 4/2001 | Hayakawa | |
| 6,228,030 B1 | 5/2001 | Urbano et al. | |
| 6,241,672 B1 | 6/2001 | Hochman et al. | |
| 6,245,017 B1 | 6/2001 | Hashimoto et al. | |
| 6,251,073 B1 | 6/2001 | Imran et al. | |
| 6,261,231 B1 | 7/2001 | Damphousse et al. | |
| 6,267,734 B1 | 7/2001 | Ishibashi et al. | |
| 6,312,382 B1 | 11/2001 | Mucci et al. | |
| 6,315,732 B1 | 11/2001 | Suorsa et al. | |
| 6,325,759 B1 | 12/2001 | Pelissier | |
| 6,344,023 B1 | 2/2002 | Fukukita et al. | |
| 6,346,079 B1 | 2/2002 | Haider et al. | |
| 6,350,238 B1 | 2/2002 | Olstad et al. | |
| 6,360,027 B1 | 3/2002 | Hossack et al. | |
| 6,379,304 B1 | 4/2002 | Gilbert et al. | |
| 6,404,428 B1 | 6/2002 | Mittelstaedt | |
| 6,425,868 B1 | 7/2002 | Tamura ....................... | 600/454 |
| 6,447,450 B1 * | 9/2002 | Olstad ........................ | 600/437 |
| 6,491,637 B2 | 12/2002 | Foster et al. | |
| 6,494,835 B1 | 12/2002 | Ciezki et al. | |
| 6,494,838 B2 | 12/2002 | Cooley et al. | |
| 6,508,768 B1 | 1/2003 | Hall et al. | |
| 6,530,887 B1 | 3/2003 | Gilbert et al. | |
| 6,540,681 B1 | 4/2003 | Cheng et al. | |
| 6,544,175 B1 | 4/2003 | Newman | |
| 6,544,187 B2 | 4/2003 | Seward | |
| 6,547,731 B1 | 4/2003 | Coleman et al. | |
| 6,558,326 B2 | 5/2003 | Pelissier | |
| 6,569,102 B2 | 5/2003 | Imran et al. | |
| 6,572,549 B1 | 6/2003 | Jong et al. | |
| 6,574,499 B1 | 6/2003 | Dines et al. | |
| 6,589,174 B1 | 7/2003 | Chopra et al. | |
| 6,629,929 B1 | 10/2003 | Jago et al. | |
| 6,638,220 B2 | 10/2003 | Satoh | |
| 6,679,845 B2 | 1/2004 | Ritter et al. | |
| 6,837,855 B1 | 1/2005 | Puech | |
| 6,923,767 B2 | 8/2005 | Saied et al. | |
| 7,052,460 B2 * | 5/2006 | Liu et al. ..................... | 600/443 |
| 2001/0031922 A1 | 10/2001 | Weng et al. | |
| 2002/0007119 A1 | 1/2002 | Pelissier | |
| 2002/0045824 A1 | 4/2002 | Cooley et al. | |
| 2002/0045825 A1 | 4/2002 | Liu et al. | |
| 2002/0050169 A1 | 5/2002 | Ritter et al. | |
| 2002/0128550 A1 | 9/2002 | Van Den Brink et al. | |
| 2002/0173719 A1 | 11/2002 | Zhao et al. | |
| 2002/0173720 A1 | 11/2002 | Seo et al. | |
| 2003/0088182 A1 | 5/2003 | He et al. | |
| 2003/0097068 A1 | 5/2003 | Hossack et al. | |
| 2003/0100833 A1 | 5/2003 | He et al. | |
| 2003/0114755 A1 | 6/2003 | Jong et al. | |
| 2003/0114759 A1 | 6/2003 | Skyba et al. | |
| 2003/0120152 A1 | 6/2003 | Omiya et al. | |
| 2003/0171668 A1 | 9/2003 | Tsujino et al. | |
| 2004/0006271 A1 | 1/2004 | Golland et al. | |
| 2004/0102704 A1 | 5/2004 | Tsujita et al. | |
| 2004/0122319 A1 | 6/2004 | Mehi et al. | |
| 2004/0267124 A1 | 12/2004 | Roundhill | |
| 2005/0010111 A1 | 1/2005 | Kristoffersen et al. | |
| 2005/0049498 A1 | 3/2005 | Roche et al. | |
| 2005/0124894 A1 | 6/2005 | Puech | |
| 2005/0203407 A1 | 9/2005 | Yoshihara et al. | |
| 2005/0240102 A1 | 10/2005 | Rachlin | |

FOREIGN PATENT DOCUMENTS

| WO | WO 2004/034694 A2 | 4/2004 |
|---|---|---|
| WO | WO2004/099814 | 11/2004 |

OTHER PUBLICATIONS

Bruining et al., "Dynamic Imaging of Coronary Stent Structures: An ECG-Gated Three-Dimensional Intracomoary Ultrasound Study In Humans." *Ultrasound Med. Biol*; 24(5):631-637 (1998).

Bruining et al., "ECG-Gated Versus Nongated Three-Dimensional Intracoronary Ultrasound Analysis: Implications for Volumetric Measurements." *Cathet. Cardiovasc. Dignosis*; 43(3):254-260 (1998).

Burckhardt, "The Performance of Mechanically Scanned Color Flow Mapping." *Ultrasound Imaging*; 11(4):227-232 (1989).

Delcker and Tegeler, "Influence of ECG-Triggered Data Acquisition on Reliability for Carotid Plaque Volume Measurements with a Magnetic Sensor Three-Dimensional Ultrasound System." *Ultrasound Med. Bio.*; 24(4):601-605 (1998).

De Korte and van der Steen A.F.W., "Intravascular Ultrasound Elastography: an Overview." *Ultrasonics*; 40(108): 859-865 (2002).

Erickson et al., Institute of Electrical and Electronics Engineers: "A Hand-Held, High Frequency Ultrasound Scanner." IEEE Ultrasonics Symposium Proceedings, Atlanta, GA; Oct. 7-10, 2001. IEEE Ultrasonics Symposium Proceedings, New York, NY; IEEE, US vol. 2 of 2; 1465-1468, Oct. 7, 2001.

Foster et al., "High Frequency Ultrasound Imaging: from Man to Mouse." *IEEE Ultrasonics Symposium*. 2:1633-1638 (2002).

Gniadecka, M., et al., "Age-Related Diurnal Changes of Dermal Oedema: Evaluation by High-Frequency Ultrasound." *Brit Jour of Derm* 131:849-855 (1994).

Gniadecka, M., et al., "Effects of Ageing on Dermal Echogenicity." *Skin Research and Tech.*, 7:204-207 (2001).

Goertz et al., "High Frequency 3-D Color-Flow Imaging of the Microcirculation." *Ultrasound Med. Biol.*; 29(1):39-51 (2003).

Goertz et al., "High Frequency Color Flow Imaging of the Microcirculation." *Ultrasound Med. Biol.*; 26(1):63-71 (2000).

Harland, C.C., et al., "Differentiation of Common Benign Pigmented Skin Lesions from Melanoma by High-Resolution Ultrasound," *Brit Jour of Derm* 143:1-10 (2000).

Kasai et al., "Real-Time Two-Dimensional Blood Flow Imaging Using an Autocorrelation Technique." IEEE Trans. Sonics Ultrasonics, 32:458-464 (1985).

Kruse et al., "A Swept-Scanning Mode for Estimation of Blood Velocity in the Microvasulature." *IEEE Trans. Ultrason. Ferroelectro. Freq. Cont.*; 45(6):1437-1998 (1998).

Loupas and Powers, "An Axial Velocity Estimator for Ultrasound Blood Flow Imaging, Based on a Full Evaluation of the Doppler Equation by Means of a Two-Dimensional Autocorrelation Approach." *IEEE trans., Ultrason. Ferroelectr. Freq. Cont.*; 42(4):672-688 (1995).

Lucassen, G.W., et al., "The Effectiveness of Massage Treatment on Cellulite as Monitored by Ultrasound Imaging." *Skin Research and Tech* 3:154-160 (1997).

Seidenari, S., et al., "Ultrasound B Scanning with Image Analysis for Assessment of Allergic Patch Test Reactions." *Contact Dermatitis*; 24:216-222 (1991).

Seidenari, S., et al., "Echographic Evaluation with Image Analysis of Normal Skin: Variations According to Age and Sex." *Skin Pharmacol*;7:201-209 (1994).

Serup, J., "Ten Years' Experience with High-Frequency Ultrasound Examination of the Skin: Development and Refinement of Technique and Equipment." *Ultrasound in Dermatology*. Berlin: Springer, 41-54 (1992).

Turnbull, "In Utero Ultrasound Backscatter Microscopy of Early Stage Mouse Embryos." *Computerized Medical Imaging and Graphics*; 23(1):25-31 (1999).

Turnbull et al., "In Vivo Ultrasound Biomicroscopy in Developmental Biology." *Trends in Biotechnology, Elsevier Publications*, Cambridge, GB 20(8):S29-S33 (2002).

Williams et al., "ECG-Triggered Retrospective Colour Flow Imaging." (Poster) INO Proceedings, Mar. 3, 2004.

Williams et al., "ECG-Triggered Retrospective Colour Flow Imaging." 2004 IEEE Ultrasonics Symp. Proc., 584-587 (Aug. 2004).

Foster, F.S., et al. "A New Ultrasound Instrument for In Vivo Microimaging of Mice", *Ultrasound in Medicine and Biology*, New York, NY, vol. 28, No. 9, Sep. 2002, pp. 1165-1172.

\* cited by examiner

SYSTEM AND METHOD FOR ECG-TRIGGERED RETROSPECTIVE COLOR FLOW ULTRASOUND IMAGING

CROSS-REFERENCE TO RELATED APPLICATIONS

This application claims the benefit of U.S. Provisional Application No. 60/549,041, filed on Mar. 1, 2004. The aforementioned application is herein incorporated by reference in its entirety.

Names of the Parties to a Joint Research Agreement

Sunnybrook and Women's College Health Sciences Centre and VisualSonics Inc. are parties to a joint research agreement.

BACKGROUND OF INVENTION

Small animal or laboratory animal research is a cornerstone of modern biomedical advancement. Research using small animals enables researchers to understand complex biological mechanisms, to understand human and animal disease progression, and to develop new drugs to cure or alleviate many human and animal maladies. Small animal research is important in many areas of biomedical research including neurobiology, developmental biology, cardiovascular research and cancer biology.

In many areas of biomedical research, accurately determining blood flow characteristics through a given organ or structure is important. For example, in the field of oncology, determination of blood flow within a tumor can enhance understanding of cancer biology and, since a tumor needs blood to grow and metastasize, help identify and develop anti-cancer therapeutics.

Color flow imaging systems estimate blood velocity by measuring the time, or frequency phase shift between backscattered signals. Color flow imaging of blood velocity in small animals such as mice and in humans has been accomplished by sweeping the transducer over a region of interest. This technique, however, has limitations including tissue clutter artifacts that are induced by the sweep velocity, which limits the ability to detect low flow rates. Other limitations include spatio-temporal decorrelation artifacts that occur when visualizing pulsatile flow, particularly if the pulse frequency is large relative to the sweep frequency of the probe. Moreover, an additional limitation includes limited accuracy of flow velocity estimation because of the number of radio frequency (RF) data lines acquired per location.

SUMMARY OF THE INVENTION

According to one embodiment a method for producing an ECG-triggered retrospective color-flow ultrasound image comprises generating ultrasound, transmitting the ultrasound into a subject at a first location, wherein a first reference point of an ECG signal taken from the subject triggers the ultrasound transmission, receiving ultrasound reflected from the subject at the first location, transmitting the ultrasound into the subject at a second location, wherein a second reference point of an ECG signal taken from the subject triggers the ultrasound transmission receiving ultrasound reflected from the subject at the second location, processing the received ultrasound to form ultrasound color traces, and reconstructing the ultrasound color traces to form the ultrasound image.

Other apparatus, methods, and aspects and advantages of the invention will be discussed with reference to the figures and to the detailed description of the preferred embodiments.

BRIEF DESCRIPTION OF THE FIGURES

The invention will be described by way of example, in the description of exemplary embodiments, with particular reference to the accompanying figures in which.

DETAILED DESCRIPTION

As used throughout, the singular forms "a," "an" and "the" include plural referents unless the context clearly dictates otherwise. Thus, for example, reference to "a trace," "a frame," or "a pulse" can include two or more such traces, frames or pulses unless the context indicates otherwise.

By a "subject" is meant an individual. The term subject includes small or laboratory animals as well as primates, including humans. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

Figure 1:
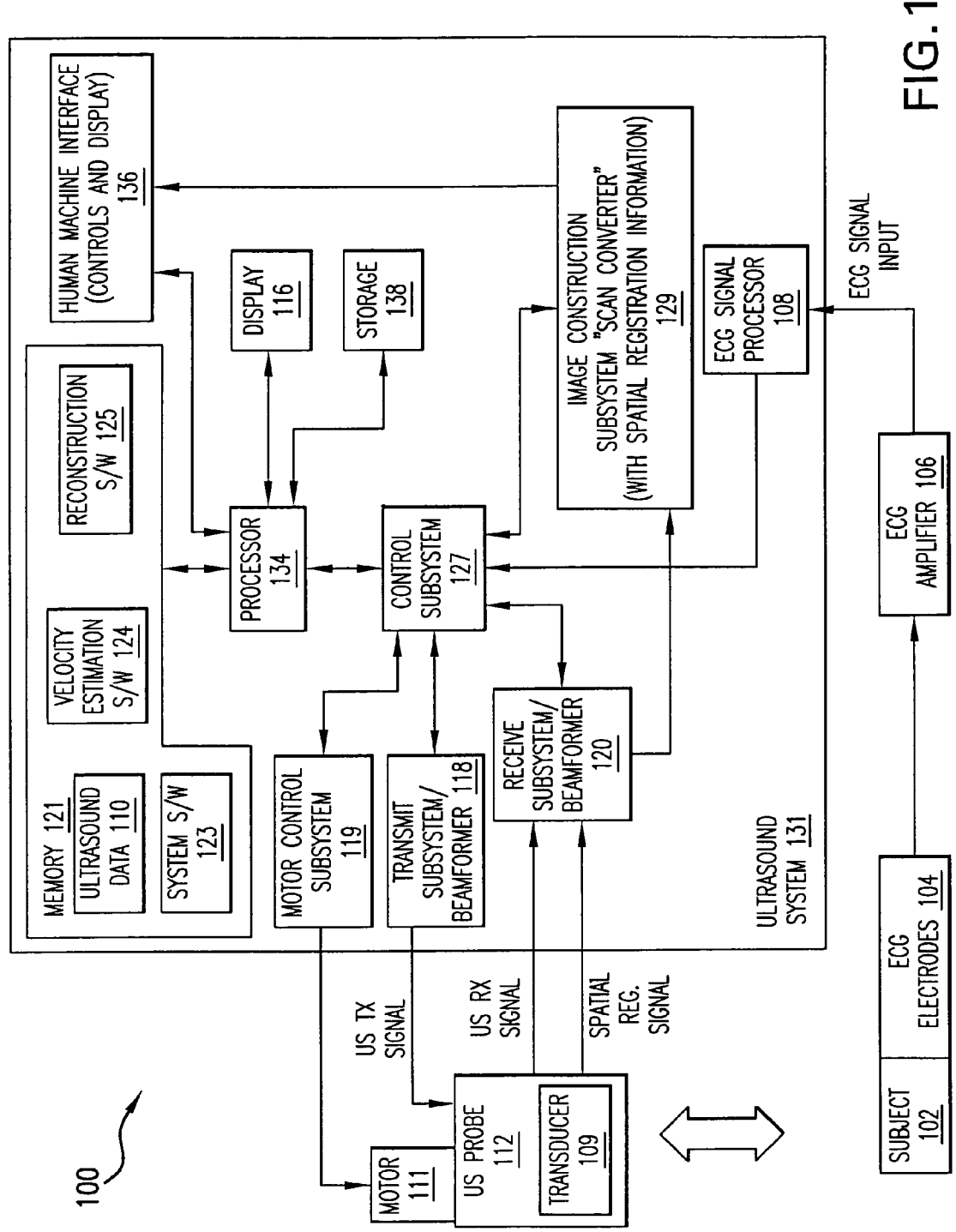
FIG. 1 is a block diagram illustrating an exemplary imaging system.

FIG. 1 is a block diagram illustrating an imaging system 100. The system 100 operates on a subject 102. An ultrasound probe 112 is placed in proximity to the subject 102 to obtain ultrasound image information. The ultrasound probe 112 can comprise a mechanically swept transducer 109 that can be used for the collection of ultrasound data 110. The transducer 109 is typically a single element mechanically scanned transducer. The ultrasound probe 112 comprises a mechanism to reposition (and record the spatial location of) the ultrasound beam. In one embodiment, the positioning mechanism comprises an optical position encoder connected to a high resolution stepping motor as described in U.S. patent application Ser. No. 10/683,890, entitled "High Frequency, High Frame-Rate Ultrasound Imaging System," which is incorporated herein by reference. In another embodiment, the transducer comprises an array of piezoelectric elements (not shown) which can be electronically steered using variable pulsing and delay mechanisms.

The transducer 109 or, if used, the array can generate ultrasound energy at high frequencies, such as, but not limited to, greater than 20 MHz and including 25 MHz, 30 MHz, 35 MHz, 40 MHz, 45 MHz, 50 MHz, 55 MHz, 60 MHz 65 MHz, 70 MHz, 75 MHz, 80 MHz, 85 MHz, 90 MHz, 95 MHz, 100 MHz and higher. Further, operating frequencies significantly greater than those mentioned above are also contemplated. The transducer 109 or, if used, the array can also generate ultrasound energy at clinical frequencies, such as, but not limited to, 1 MHz , 2 MHz, 3 MHz, 4 MHz, 5 MHz, 10 MHz or 15 MHz. These disclosed high and clinical frequencies refer to exemplary nominal center frequencies at which the transducer 109 or array can generate and transmit ultrasound energy. As would be clear to one skilled in the art, such frequencies can vary.

The subject 102 is connected to electrocardiogram (ECG) electrodes 104 to obtain a cardiac rhythm or signal (FIG. 3) from the subject 102. The cardiac signal from the electrodes 104 is transmitted to an ECG amplifier 106 to condition the signal for provision to an ultrasound system 131. It is recognized that a signal processor or other such device can be used instead of an ECG amplifier to condition the signal.

If the cardiac signal from the electrodes 104 is suitable as obtained, then use of an amplifier 106 or signal processor could be avoided entirely.

The ultrasound system 131 includes a control subsystem 127, an image construction subsystem 129, sometimes referred to as a "scan converter," a transmit subsystem/beamformer 118, a receive subsystem/beamformer 120, a motor control subsystem 119 and a user input device 136. Beamformers are used if the transducer comprises an electronically steerable array. The processor 134 is coupled to the control subsystem 127 and the display 116.

A memory 121 is coupled to the processor 134. The memory 121 can be any type of computer memory, and is typically referred to as random access memory "RAM," in which the system software 123, velocity estimation software 124 and retrospective reconstruction software 125 of the invention resides. The system software 123, velocity estimation software 124, and retrospective reconstruction software 125, control the acquisition, processing and display of the ultrasound data 110 allowing the ultrasound system 131 to display a retrospective color flow image. The system software 123, velocity estimation software 124, and retrospective reconstruction software 125, comprise one or more modules to acquire, process, and display data from the ultrasound system 131. The software comprises various modules of machine code which coordinate the ultrasound subsystems.

Data is acquired from the ultrasound system, processed to form images, and then displayed on a display 116. The system software 123, velocity estimation software 124, and retrospective reconstruction software 125, allow the management of multiple acquisition sessions and the saving and loading of data associated with these sessions. Post processing of the ultrasound data to obtain an image is also enabled through the system software 123, velocity estimation software 124, and retrospective reconstruction software 125.

The system for ECG-triggered retrospective color flow imaging can be implemented using a combination of hardware and software. The hardware implementation of the system can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the system comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic) a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The memory 121 can include the ultrasound data 110 obtained by the imaging system 100. A computer readable storage medium 138 is coupled to the processor for providing instructions to the processor to instruct and/or configure processor to perform steps or algorithms related to the operation of the ultrasound system 131. The computer readable medium can include hardware and/or software such as, by way of example only, magnetic disks, magnetic tape, optically readable media such as CD ROM's, and semiconductor memory such as PCMCIA cards. In each case, the media may take the form of a portable item such as a small disk, floppy diskette, cassette, or it may take the form of a relatively large or immobile item such as hard disk drive, solid state memory card, or RAM provided in the support system. It should be noted that the above listed example mediums can be used either alone or in combination.

Figure 8:
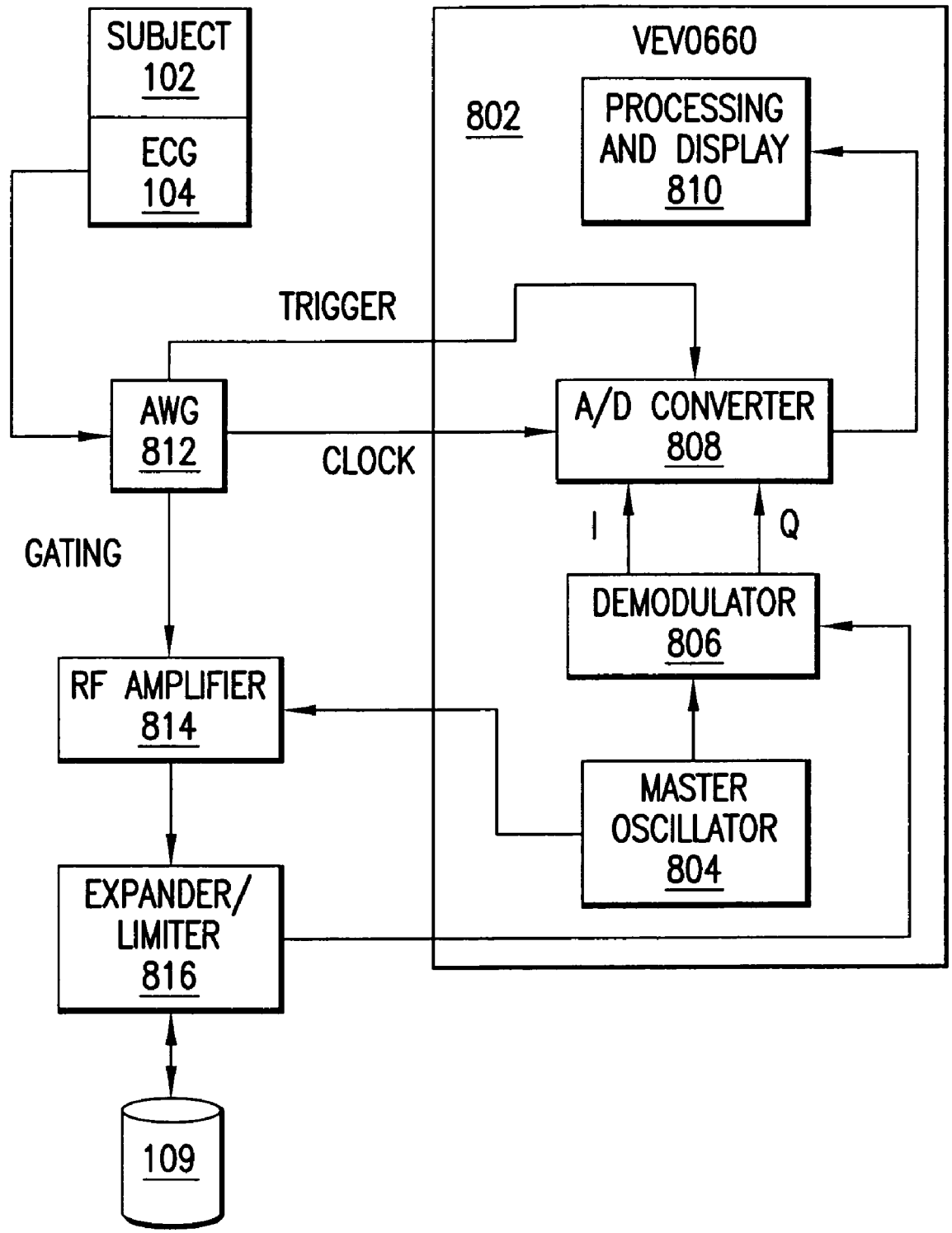
FIG. 8 is a block diagram illustrating an exemplary retrospective color flow imaging system.

The ultrasound system 131 can include a control subsystem 127 to direct operation of various components of the ultrasound system 131. The control subsystem 127 and related components may be provided as software for instructing a general purpose processor or as specialized electronics in a hardware implementation. In one embodiment, the control subsystem 127 can include a master oscillator 804 (FIG. 8) which can generate a continuous wave (CW) signal for provision to the transmit subsystem 118.

The control subsystem 127 is connected to a transmit subsystem/beamformer 118 to provide an ultrasound transmit signal to the ultrasound probe 112. The transmit subsystem 118 can be internal to the ultrasound system 131 as shown in FIG. 1. In one embodiment, portions of the transmit subsystem 118 can be external to the ultrasound system 131. For example, in one embodiment, an arbitrary waveform generator (AWG) 812 (FIG. 8) and an RF amplifier 814 (FIG. 8) can be used to provide the transmit signal to the ultrasound probe 112. The transmit subsystem 118 causes the transducer 109 to transmit a number of ultrasound pulses 402 (FIG. 4) into the subject 102. Multiple pulses can be transmitted and are referred to through out as a "pulse train." A "pulse train" or "train" can comprise about, for example, 500, 1000, 2000, 3000, 4000, 5000, 10,000 or more pulses per second. The number of pulses in a pulse train or train can vary, however, as would be clear to one skilled in the art.

The ultrasound probe 112 provides an ultrasound receive signal to a receive subsystem/beamformer 120. The receive subsystem 120 also provides signals representative of the received signals to the image construction subsystem 129. In one embodiment, the receive subsystem 120 can include a demodulator 806 (FIG. 8) and an analog-to-digital (A/D) converter 808 (FIG. 8), which can condition the received ultrasound signal for provision to the control subsystem 127 and the image construction system 129. The demodulator 806 is an element that uses the envelope of an RF data signal received from the transducer 109 and converts it into an in-phase (I) and quadrature-phase (Q) format. The I and Q data from the demodulator 806 can be converted into digital data by the analog to digital converter 808 for provision to the control subsystem 127 and the image construction subsystem 129. In other embodiments, rather than the envelope being sampled to produce I and Q data, the RF signal can be sampled directly by methods known in the art.

The ultrasound system 131 includes an image construction subsystem 129 for converting the electrical signals generated by the received ultrasound echoes to data that can be manipulated by the processor 134 and that can be rendered into an image on the display 116. The image construction subsystem 129 is directed by the control subsystem 127 to operate on the received data to render an image for display using the ultrasound data 110. The control subsystem 127 is also coupled to a motor control subsystem 119 to provide a motor control signal to the motor 111 to control the movement of the ultrasound probe 112 to a location K (FIG. 2) on the subject 112, as described below. The image construction subsystem 129 is directed by the control subsystem 127.

The ultrasound system 131 can include an ECG signal processor 108 configured to receive signals from the ECG amplifier 106. The ECG signal processor 108 provides various signals to the control subsystem 127. The ECG signal can be used to trigger transmission by the transducer 109 of a number of pulses of ultrasonic energy, or pulse train. The signals provided to the control subsystem 127 from the ECG signal processor 108 can trigger the acquisition of ultrasound data 110 across a region of anatomy of a subject 102.

In another embodiment, rather than triggering the transmission of ultrasonic energy, the receive subsystem 120 can also receive an ECG time stamp from the ECG signal processor 108 as described in U.S. patent application Ser. No. 10/736,232 entitled "System of Producing an Ultrasound Image using Line-Based Image Reconstruction," which is incorporated herein by reference. In this incorporated embodiment, the ECG signal is not used to trigger the transmission of pulses, but instead the ECG is recorded continuously and simultaneously with the ultrasound data 110. From the recorded ECG signal, a series of time stamps are selected and used to determine which of the RF data collected at each location will be used to reconstitute the first frame of a cineloop, and from there, the subsequent frames. As used throughout this document, a cineloop is a movie comprising a series of images displayed at a relatively high frame-rate.

The ultrasound system 131 transmits and receives ultrasound data through the ultrasound probe 112, provides an interface to a user to control the operational parameters of the imaging system 100, and processes data appropriate to formulate an ECG-triggered retrospective color flow image. As used throughout this document, an ECG-triggered retrospective color flow image is an image comprising an image of flow (i.e. bloodflow) over a region of interest at a specific time relative to the cardiac cycle of a subject 102, reconstructed from a set of data acquired upon the detection of a trigger signal detected from the subject's EGC trace. Images are presented through the display 116. A series of images can be presented on the display 116 as a cineloop.

The human-machine interface 136 takes input from the user, and translates such input to control the operation of the ultrasound probe 112. The human-machine interface 136 also presents processed images and data to the user through the display 116.

The system software 123, the velocity estimation software 124 and the retrospective reconstruction software 125, in cooperation with the image construction subsystem 129 operate on the electrical signals developed by the receive subsystem 120 to develop an ECG-triggered retrospective color flow image of anatomy of the subject 102.

The system software 123 can, in cooperation with the processor 134, direct the acquisition of the ultrasound data 110, as described below. The velocity estimation software 124 in cooperation with the processor 134 and the acquired ultrasound data 110, can process the acquired data to provide a velocity estimate, or color flow traces, as will be described below. The velocity estimation software 124 can process the ultrasound data using, for example, the Kasai autocorrelation color flow technique as described, for example, by Loupas et al. IEEE Trans. Ultrason. Ferroelectr. Freq. Cont. 42(4): 672-687 (1995). The velocity estimation software 124 can also process the ultrasound data 110 using a cross-correlation method, a Fourier method, or by using other methods known in the art. The retrospective reconstruction software 125, in cooperation with the processor 134, the velocity estimates produced by the velocity estimation software 124, and the image construction subsystem 129 can produce a color flow retrospective reconstruction image of the acquired and processed data to be displayed on the display 116, as described below. A reconstructed image can be displayed on the display 116 and a series of images can be played as a movie or cineloop.

A method of using the imaging system 100 described above to produce an ECG-triggered retrospective color flow ultrasound image can comprise data acquisition, color flow processing, and color flow reconstruction.

Figure 2:
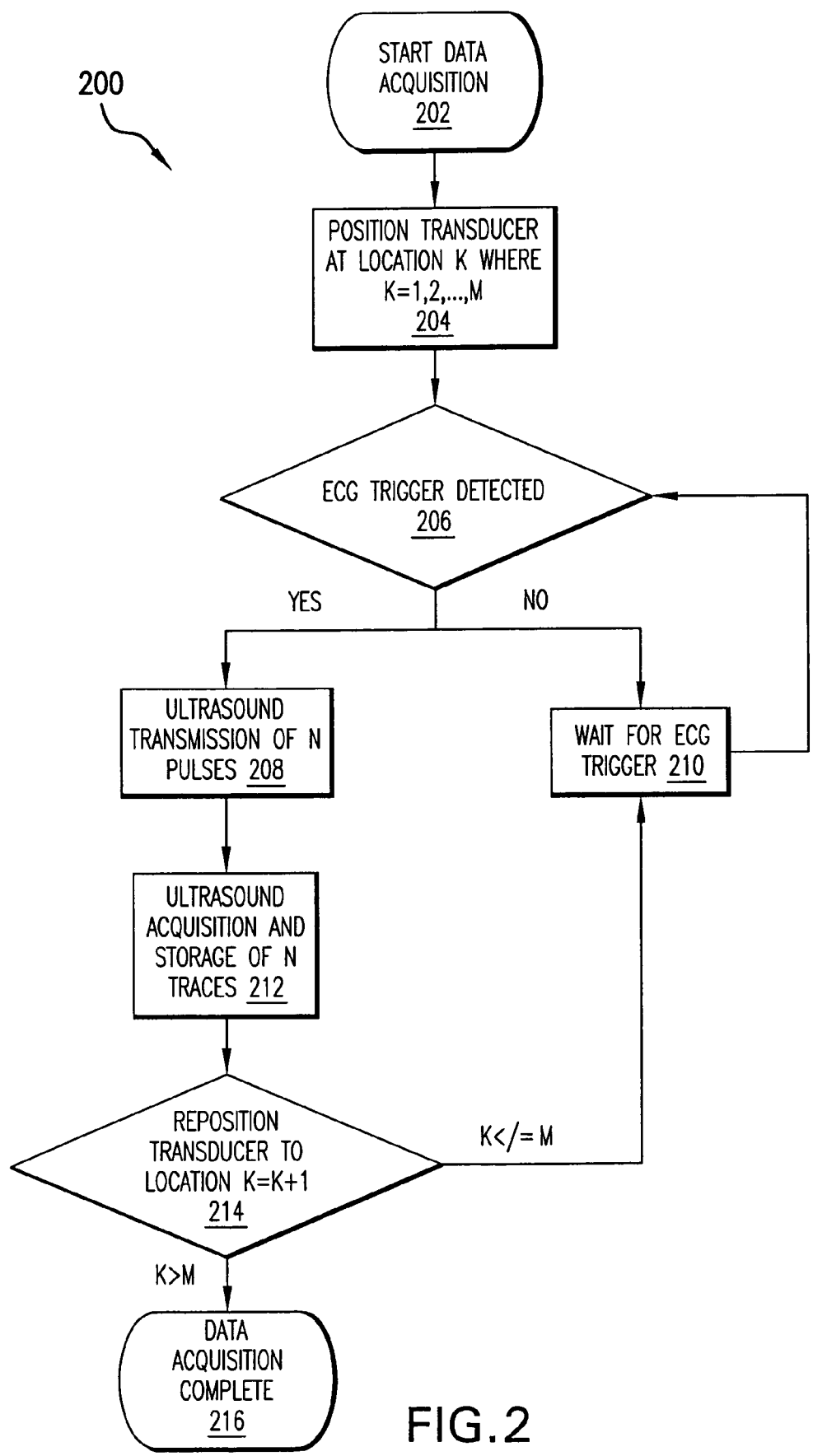
FIG. 2 is a flowchart illustrating the operation of ultrasound data acquisition by an exemplary imaging system for producing an ECG-triggered retrospective color flow ultrasound image.

FIG. 2 is a flowchart 200 illustrating the operation of an embodiment of the ultrasound data 110 acquisition by the imaging system 100 for producing an ECG-triggered retrospective color flow ultrasound image. The blocks in the flow chart may be executed in the order shown, out of the order shown, or concurrently. In block 202, the imaging system 100 begins the process of data acquisition. In block 204, the ultrasound probe 112 including the transducer 109 is positioned relative to a subject 102 at a location K where K=1,2, . . . M. At each location K, RF data is acquired using a pulse-echo technique.

The ultrasound probe 112 can be initially positioned at location K=1, manually or by using the motor 111, which is under the control of the motor control subsystem 119, the control subsystem 127, and the system software 123. The location K=1 corresponds to a portion of a subject's 102 anatomy where a first ultrasound signal is transmitted and received. Each subsequent value of K, K=2,3, . . . M, corresponds to a subsequent location corresponding to portions of the subject's 102 anatomy where subsequent ultrasound signals are transmitted and received, as described below.

Each value of K can correspond to a lateral location along a subject 102, separated by a given distance. For example, each location K may be separated by approximately 1 micrometer (μm), 5 μm, 10 μm, 15 μm, 20 μm, 25 μm, 30 μm, 35 μm, 40 μm, 45 μm, 50 μm, 100 μm, 500 μm or more. The ultrasound probe 112 can be positioned at each location K, and moved between each location K, based on the user's input at the human machine interface 136 and through use of the motor 111, which is under control of the motor control subsystem 119 and the system software 123.

The distance between each location K may be chosen by a user and input by the user at the human machine interface 136. The distance between each location K is typically referred to as "step size." Choices regarding step size can be made by one skilled in the art, and generally relate to factors including the width of the emitted ultrasound beam, the size of the region or portion of a subject's anatomy to be imaged and/or the blood or fluid flow characteristics through the region or portion of the subject's anatomy to be imaged. For example, one of skill in the art may choose a step size such that a sufficient number of locations K are defined across a region of a subject's anatomy. Thus, if a small region of a subject's anatomy is imaged, a small step size may be used so that ultrasound can be transmitted at a sufficient number of locations K along the region. One skilled in the art may also choose a step size based on the differences in blood flow velocity within the region or portion of the subject's anatomy being imaged. For example, if velocity changes rapidly within the region, a smaller step size may be chosen than if velocity is relatively uniform throughout the region.

Figure 3:
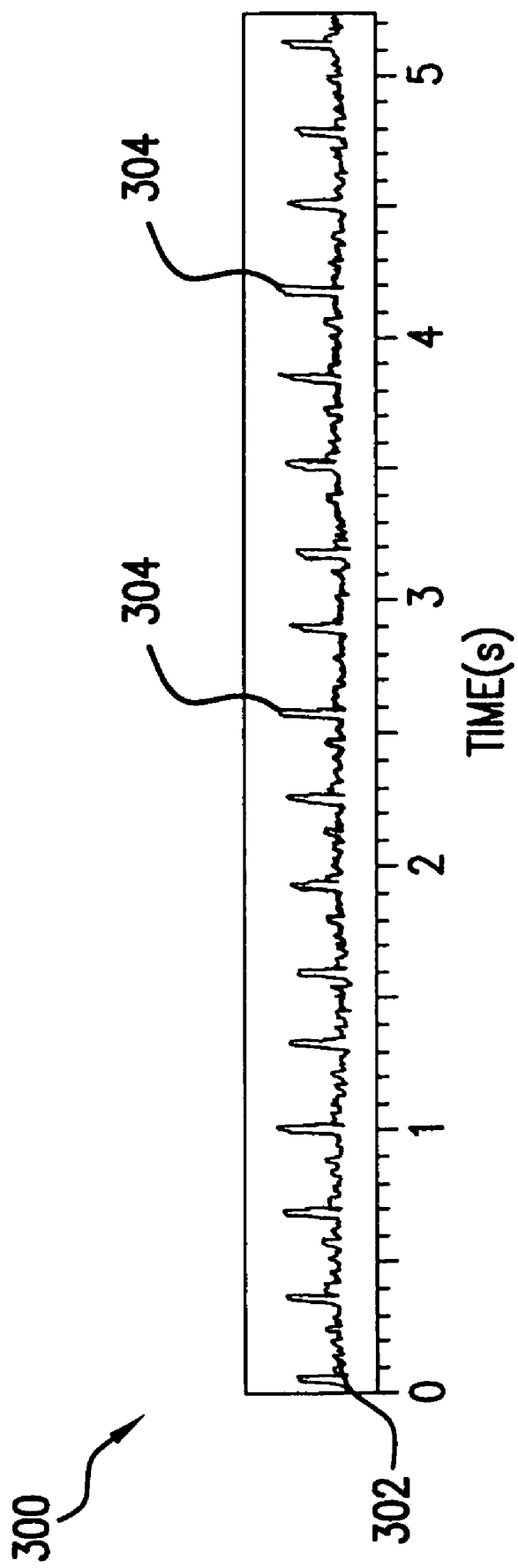
FIG. 3 shows an exemplary ECG signal from an exemplary subject.

In block 206, the ultrasound system 131 detects an ECG trigger from the ECG signal processing module 108. The ECG trigger is based on a subject's 102 ECG signal, which is provided to the ECG signal processing module 108 though use of ECG electrodes 104 and the ECG amplifier 106. An exemplary ECG signal is shown in FIG. 3 by the numeral 300. The ECG signal is represented by the trace 302. The ECG processing module 108 of the ultrasound system 131 automatically detects, using peak detection of the R-wave pulse 304, a fixed and repeatable point on the ECG signal trace 302 from which the transmission of an ultrasound transmit signal or pulse can be triggered. Thus, in block 206, whether a peak of the R-wave pulse 304 has occurred (representing the ECG trigger) is determined. Other waves, or peaks thereof, of the subject's ECG signal trace 302 can also be used to trigger an ultrasound transmit signal or pulse. For example, the P-wave, Q-wave, S-wave, and T-wave or peaks thereof can be used to trigger the acquisition. Each wave referred to above can represent a reference point which can trigger the transmission of ultrasound energy. An ECG signal trace 302 can comprise multiple peaks of each wave and each peak can trigger the transmission of ultrasound energy. Thus an ECG trace can comprise a first and a second, or more of the above described wave peaks. Each peak can provide a reference point of the ECG signal for triggering transmission of ultrasound energy. When a peak of a given wave type is selected to trigger the transmission of ultrasound energy, subsequent peaks of the same wave type can be used to trigger subsequent transmissions of ultrasound energy.

If an ECG trigger is detected in block 206, then the transmit subsystem 118 causes the transmission of N pulses of ultrasound energy from the transducer 109 into the subject 102 in block 208. The transmission of N pulses (pulse-train) is triggered by an ECG signal acquired from the subject being imaged. The transmit pulse-train comprises a number of transmission pulses (1 to N), with a maximum pulse repetition frequency (PRF) determined by the distance from the transducer to the flow being imaged and the properties of the portion of the anatomy (i.e. speed of sound and maximum flow velocity) of the subject 102 being imaged. At a PRF of 10 kHz, 10,000 pulses per second are transmitted at each transducer 109 location. The PRF may be lowered from the maximum possible value in accordance with the flow velocities to be imaged. For example, using a 40 MHz pulse with a 10 kHz PRF, aliasing of flow occurs when detecting axial velocities of greater than 100 millimeters per second (mm/s). A region of slower flow allows for a lower PRF to be used, depending on the desired velocity resolution. A higher PRF can be used to produce a higher frame-rate in the resulting retrospective color flow cineloop. The maximum possible frame-rate is equal to the PRF. For each location, the received pulses (1 to N), in the form of RF data are converted to I and Q data by the receive subsystem 120 and are stored in demodulated I and Q form in the memory 121 as ultrasound data 110. Ultrasound data 110 can also be stored in RF form. When storing ultrasound data 110 in RF form a higher frame acquisition sampling frequency can be used.

If an ECG trigger is not detected in block 206, then the ultrasound system 131 waits for the ECG trigger in block 210. In block 212, for each pulse of ultrasound energy N transmitted by the transducer an echo of RF ultrasound energy is received by the transducer 109 and provided to the ultrasound system 131 using the receive subsystem 120. This received ultrasound energy is collected and stored as N traces of demodulated ultrasound data 110.

In block 214, the ultrasound probe 112, including the transducer 109, is repositioned to a new location K along the subject 102 where K=K+1. If, in block 214, K is greater than M, then data acquisition is complete in block 216. If, in block 214, K is less than or equal to M then data acquisition is not complete, and the ultrasound system 131 waits for a subsequent ECG trigger at block 210.

Figure 4:
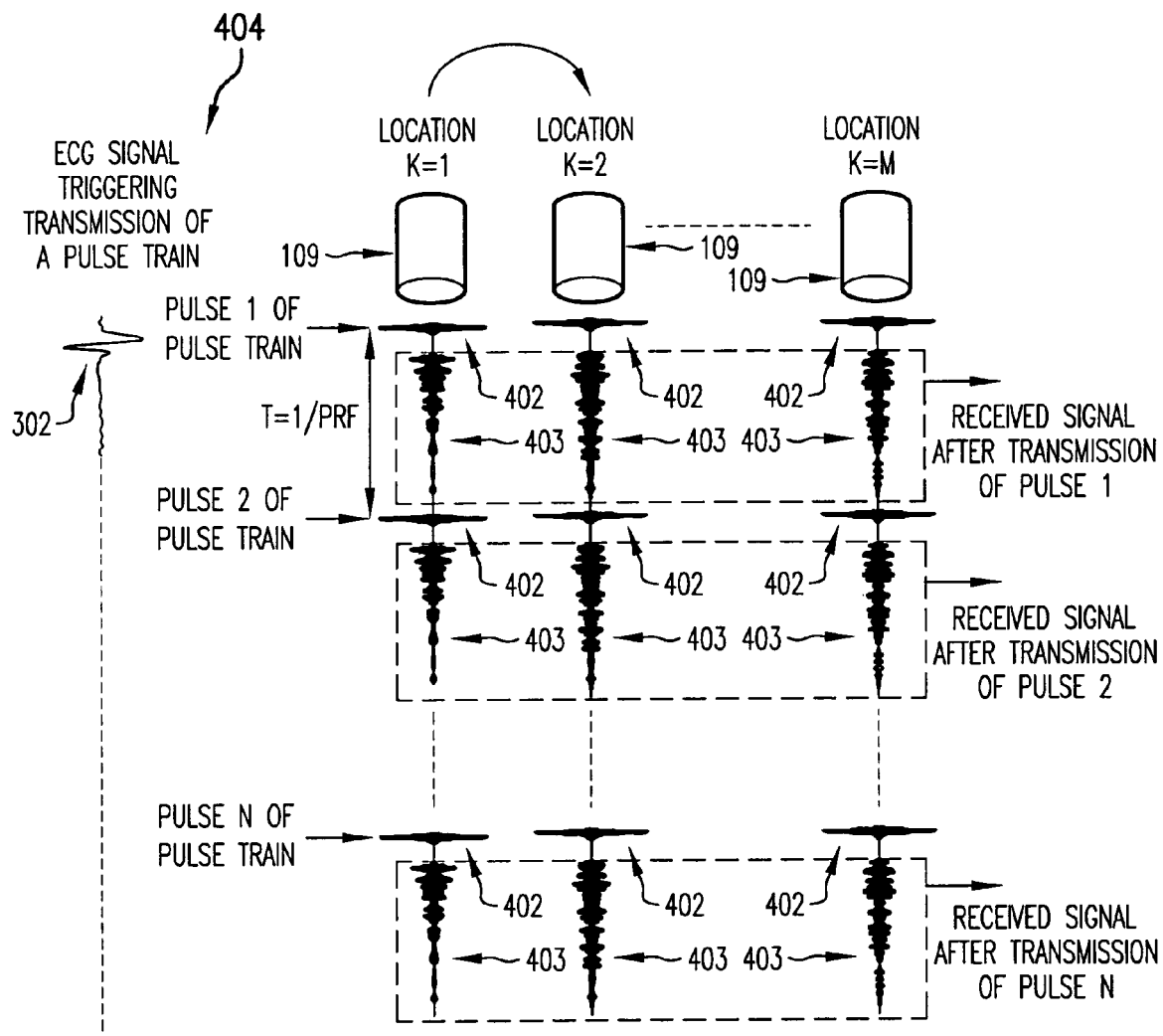
FIG. 4 is a schematic diagram illustrating the acquisition of ultrasound data using an exemplary imaging system for producing an ECG-triggered retrospective color flow ultrasound image.

FIG. 4 is a schematic diagram illustrating the acquisition of ultrasound data 110 using the imaging system 100 for producing an ECG-triggered retrospective color flow ultrasound image. FIG. 4 shows locations K (K=1,2, . . . M) for the ultrasound transducer as described above and as detailed in flow chart 200. At each location K=1,2, . . . M, the transducer 109 transmits a train of N ultrasound pulses (1 to N) 402, which are separated by a time T=1/PRF, into a subject 102 and receives RF echoes 403 after transmission of each pulse 402. The train of N pulses 402 are transmitted based on an ECG trigger signal 404 derived from an ECG trace 302 from a subject 102.

Figure 5:
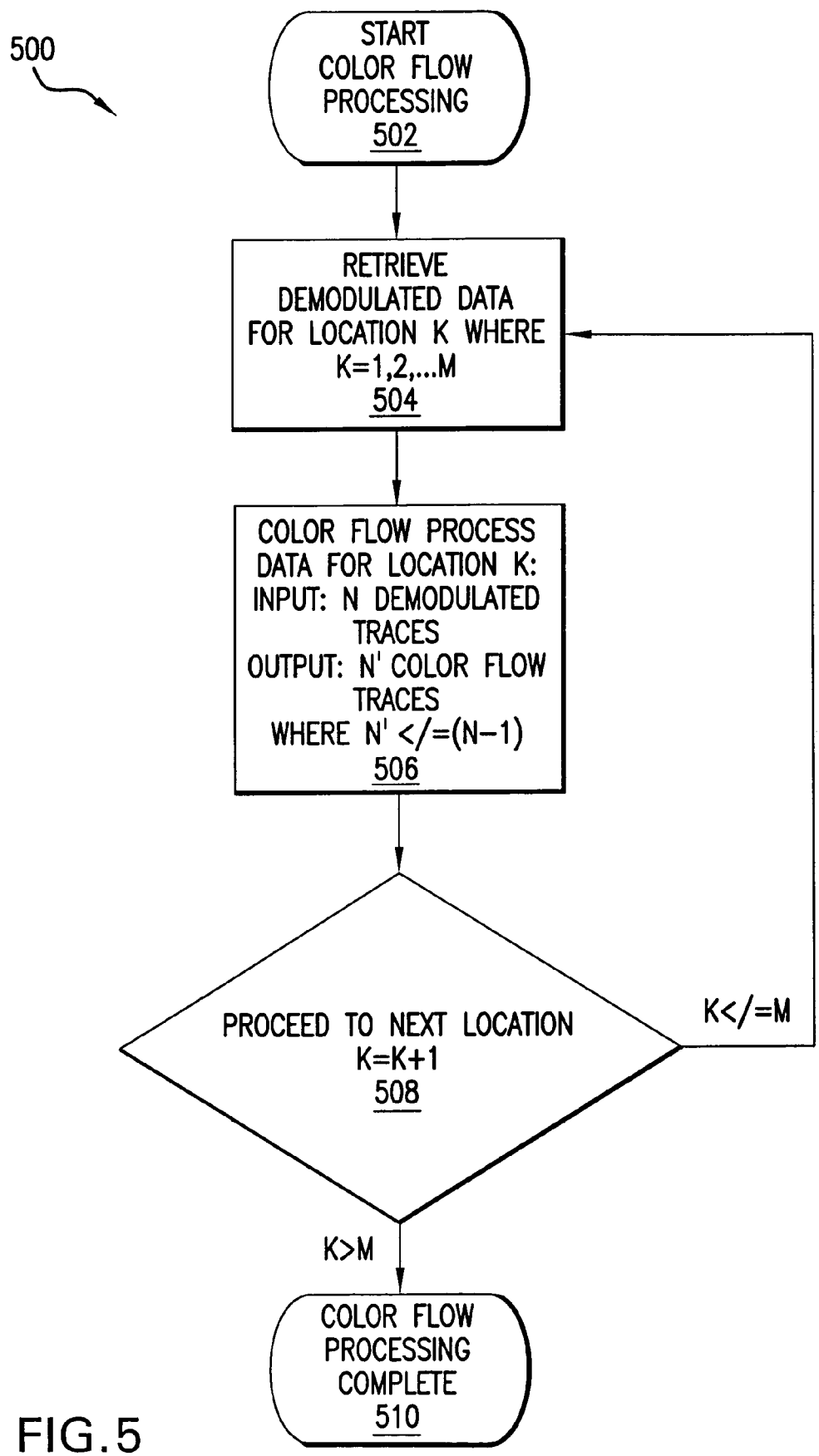
FIG. 5 is a flowchart illustrating the operation of color flow processing by an exemplary imaging system for producing an ECG-triggered retrospective color flow ultrasound image.

FIG. 5 is a flowchart 500 illustrating the operation of color flow processing by the imaging system 100 for producing an ECG-triggered retrospective color flow ultrasound image. The blocks in the flow chart may be executed in the order shown, out of the order shown, or concurrently. In block 502, the ultrasound system 131 begins color flow processing. The ultrasound data 110 acquired at each location K is processed from N traces of demodulated I and Q data to N' color flow traces. The number of color flow traces is typically less than or equal to N minus 1, depending on the size of the ensemble used in the color flow processing. An ensemble is a group of successive RF lines used to generate one color flow trace.

Color flow processing is performed by velocity estimation software 124 in conjunction with the processor 134 and the acquired and collected ultrasound data 110. In block 504, ultrasound data 110 is retrieved for a location K where K=1,2, ... M. In block 506, ultrasound data 110 for a location K is input into the velocity estimation software 124 as N demodulated traces. The velocity estimation software 124 takes the input of N demodulated traces, and outputs N' color flow traces, where N' is less than or equal to N minus 1.

Velocity estimation software 124 performs a correlation of velocity estimate on the input N traces collected at each location K. To perform the correlation velocity estimate, the velocity estimation software 124 can use, for example, the Kasai autocorrelation color flow technique as described in Loupas et al. IEEE Trans. Ultrason. Ferroelectr. Freq. Cont. 42(4): 672-687 (1995), which is incorporated herein by reference. Other methods of velocity estimation can be used, however. For example, a cross correlation method, or a Fourier method, which is known in the art, can be used. In block 508, ultrasound data 110 is retrieved for the location K=K+1. If, in block 508, the new value of K is greater than M, color flow processing is compete at block 510. If, in block 508, the new value of K is less than or equal to M then processing as described in block 504 and 506 for the location K=K+1 is performed.

Figure 6:
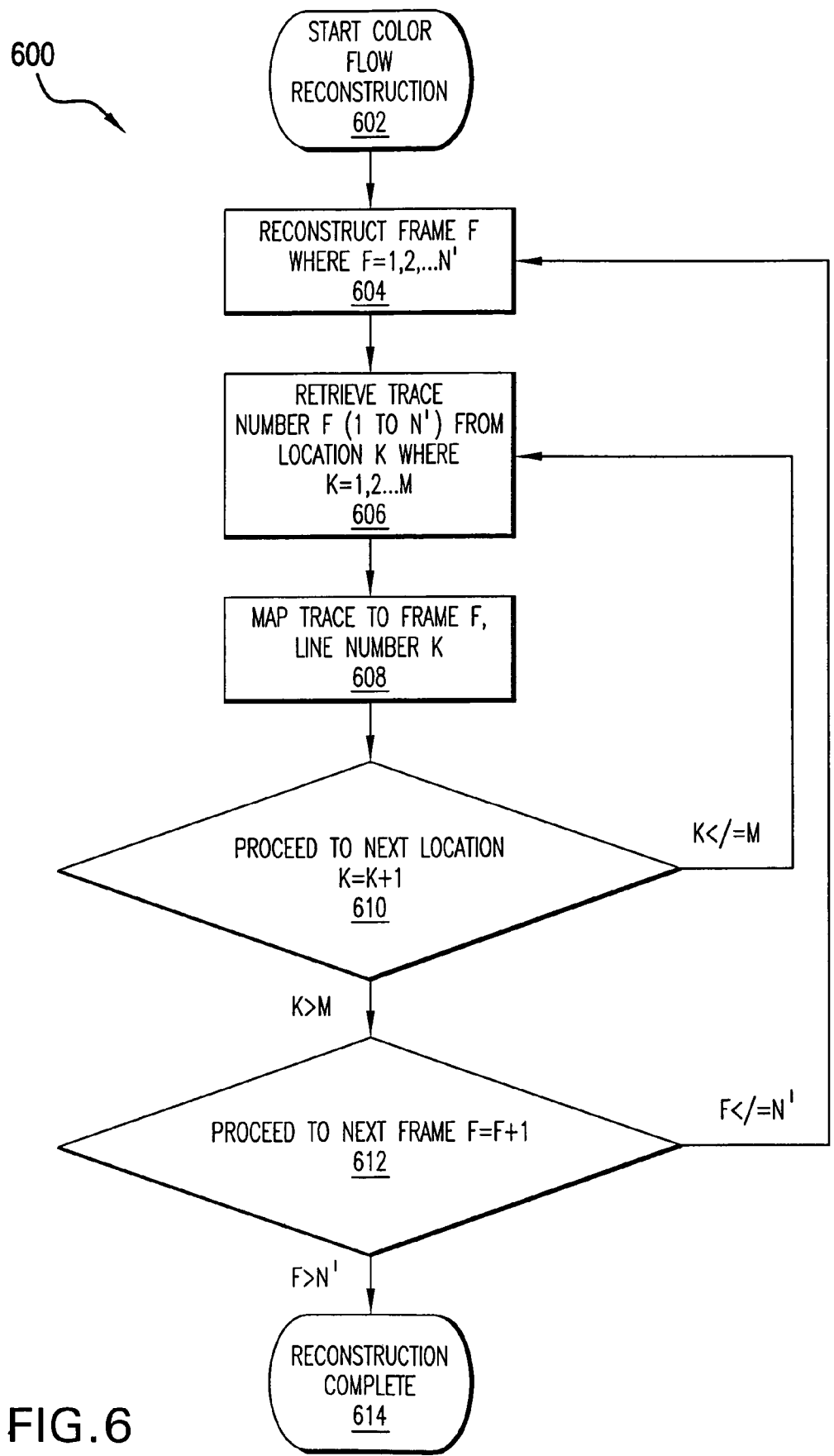
FIG. 6 is a flowchart illustrating the operation of color flow reconstruction by an exemplary imaging system for producing an ECG-triggered retrospective color flow ultrasound image.

FIG. 6 is a flowchart 600 illustrating the operation of color flow reconstruction by the imaging system 100 for producing an ECG-triggered retrospective color flow ultrasound image. The blocks in the flow chart may be executed in the order shown, out of the order shown, or concurrently. Color flow image reconstruction is directed by retrospective reconstruction software 125 that maps the color flow processed traces N' produced by the velocity estimation software 124 that correspond to the N traces of RF data acquired at each transducer location (K=1,2, ... M) into a representation of the flow over the region or portion of a subject's anatomy.

In block 602, the ultrasound system 131 begins color flow reconstruction. In block 604, retrospective reconstruction software 125 reconstructs a frame F where F=1,2, ... N'. The number of frames N' in the reconstructed color flow reconstruction is determined by the number of color flow processed traces, N', which is the output of block 506.

Figure 7:
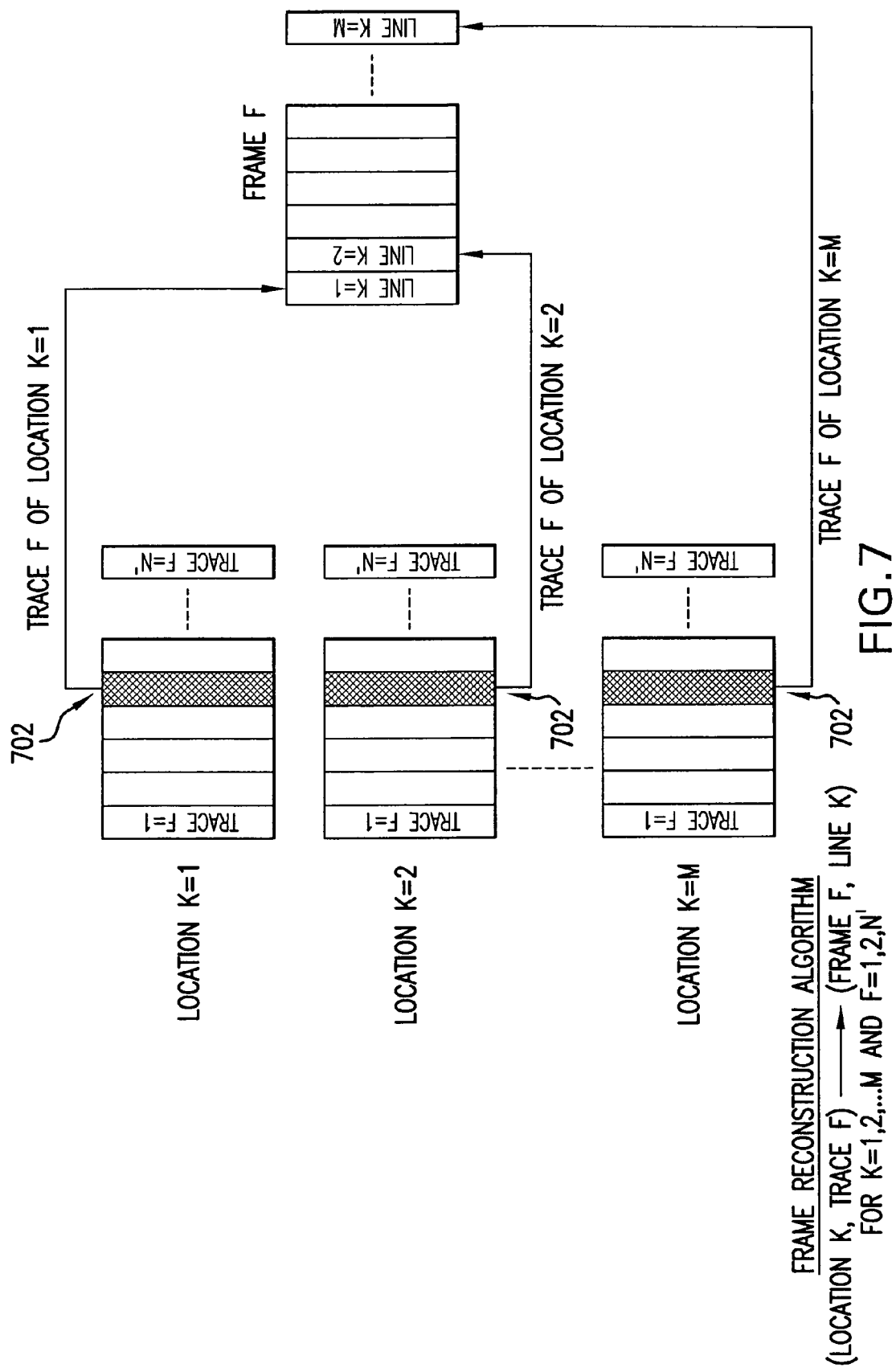
FIG. 7 is a schematic diagram illustrating retrospective color flow reconstruction.

In block 606, retrospective reconstruction software 125 retrieves color flow trace number F (1 to N') corresponding to an RF data ensemble taken from the transducer location K where K=1,2, ... M. In block 608, each trace number F from each location K is mapped by the retrospective reconstruction software 125 to frame number F as line 702 number K (K=1, 2, ... , M) (FIG. 7). The number of lines 702 that comprise each frame F is determined by the number of transducer locations, M, over which data was acquired.

In block 610, the retrospective reconstruction software 125 proceeds to the next location K=K+1 and determines if K is greater than M or if K is less than or equal to M. If K is greater than M, then in block 612 the retrospective reconstruction software 125 proceeds to reconstruct the next frame F=F+1. If, in block 610, K is less than or equal to M then a subsequent trace number N' is retrieved as described in block 606. In block 612, the retrospective reconstruction software 125 determines if the frame number F reconstructed is greater than the number of color flow traces N' in block 604 where F=1,2, ... N'. If F is grater than N', then the reconstruction is complete at block 614. If F is less than or equal to N', then a subsequent frame is constructed in block 604. Thus, the retrospective reconstruction software 125 proceeds by inserting color flow trace number, F (1 to N'), processed from an ensemble of RF traces acquired at transducer location, K, into line (1 to M) of frame F(1 to N').

FIG. 7 is a schematic diagram illustrating retrospective color flow reconstruction. After data acquisition at all locations K (K=1,2, ... M), and data processing to produce N' color flow traces per location K, color flow frame number F (F=1,2, ... N') is reconstructed by placing the color flow trace number F (F=1,2, ... N') produced at each location K (K=1,2, ... M) into line number K of frame number F. After reconstruction of the frames F (1 to N'), a plurality of frames can be assembled from the frames and displayed in series as a cineloop. For example, a cineloop can be assembled beginning with frame 1 and ending with frame N', showing blood flow in the subject.

As described above, the transmitted ultrasound of the disclosed system may vary in frequency. The desired frequency is based on the imaging technique to which the system and method is applied, and can be determined by one having ordinary skill in the art. For example, depending on the anatomy, size, and depth of an object or blood flow to be imaged in a subject, a certain frequency may be chosen for imaging at that desired size and depth. Choosing a particular ultrasound frequency for imaging at a desired size or depth in a subject could be determined readily by one having ordinary skill in the art. Similarly, the PRF may be chosen in accordance with the distance of the flow from the transducer 109, and the flow velocities to be imaged. A higher PRF is used with higher flow velocities to prevent aliasing in the color flow velocity estimation.

The traces are implicitly aligned with one another due to correlation of the ECG trigger signal 404 (FIG. 4) with pulsatile flow of blood through the vasculature of the subject 102. The frequency of pulsatile flow of blood is naturally correlated to the frequency of a contracting and expanding object, such as a beating heart. By triggering the ultrasound transmission and RF data acquisition using the ECG signal trigger, color flow can be estimated at each location K of a subject 102 at the same time point relative to the pulsatile flow cycle, over a range of time points.

The system and method described herein may also be used in conjunction with contrast agents, including microbubble contrast agents and targeted microbubble contrast agents as described in U.S. patent application Ser. No. 11/040,999 entitled "High Frequency Ultrasound Imaging Using Contrast Agents," which is incorporated herein by reference.

An ECG-triggered retrospective color flow image produced as described above can be overlaid on a retrospective B-scan image using overlaying methods known in the art. For example, an ECG triggered retrospective color flow image can be overlaid on image produced using line based reconstruction as described in U.S. patent application Ser. No. 10/736,232, entitled "System for Obtaining an Ultrasound Image Using Line-Based Image Reconstruction," which is incorporated herein by reference. For example, a first image of a portion of anatomy of a subject 102 can be produced using the incorporated line based reconstruction method. ECG-triggered retrospective color flow data or images can be overlaid onto the first image. The overlaid color flow images correspond to a region of interest within the portion of anatomy depicted in the first image produced by the line based reconstruction method. Thus, ECG-triggered retrospective color flow image indicating velocity of flow can be laid over the image of the underlying portion of anatomy produced by the line based reconstruction technique. For example, ECG-triggered color flow image reconstruction images of blood flow in a vessel can be laid over the line based reconstruction image of the vessel anatomy. The ECG-triggered retrospective color flow image can also be laid over retrospective B-scan images produced using a method as described below in example 1.

EXAMPLES

The following examples are intended to be purely exemplary of the invention and are not intended to limit the scope of what the inventors regard as their invention.

Example 1

In Vivo Carotid Imaging Using ECG-triggered Retrospective Color Flow Imaging For swept-scan data acquisition, a Vevo660 ultrasound biomicroscope (UBM) system 802 (FIG. 8)(Visualsonics, Toronto, ON, Canada) was used to transmit and receive ultrasound data. The system was set to generate seven cycle pulses by internally gating and amplifying the CW signal produced by a master oscillator 804.

For in vivo carotid imaging, 40 MHz pulses were transmitted by an ultrasound probe 112 with a transducer 109. For example, an RMV604 probe equipped with a 40 MHz transducer (6 mm focal length) at a PRF of 10 kHz was used. For color flow imaging, received signals were demodulated using a demodulating element 806 by the Vevo660 802 using the CW signal from its master oscillator 804 to produce in-phase (I) and quadrature-phase (Q) signals that were digitized by an analog to digital converter (A/D) 808.

Transmitted pulses were generated using the CW signal provided by the master oscillator 804 of the Vevo660 802, which was externally gated and amplified by an RF power amplifier 814 (M3206, AMT, Anaheim, Calif.). The gating signal, comprising a train of 10,000 rectangular pulses equally time spaced by 100 µm (PRF=10 kHz), was provided by the arbitrary waveform generation AWG 812 (AWG 2021, Tektronix, Beaverton Oreg.). Received signals were demodulated internally by the Vevo660 802. The gating signal provided by the AWG 812 was also used to trigger data acquisition by the A/D board 802, at a sampling clock provided by the AWG 812.

For data acquisition, the transducer was kept fixed at successive positions relative to the subject's (mouse) tissue. At each position, a 10,000 pulse train was transmitted and data were collected before moving the transducer to the next position. The transmission of the pulse train was triggered by the ECG signals from the mouse heart rate by a monitoring system. The monitoring system can comprise ECG electrodes 104, an ECG amplifier 106, and an ECG signal processor 108 as described above. Assuming a periodic trigger from the ECG signal from the mouse, data collected after transmission of the pulse number n ($1 \leq n \leq 10,000$) at each location were acquired at the same period of the subject's 102 heart cycle. An expander and limiter element 816 can also be used. The expander can be used to prevent low amplitude transmitted electronic noise from interfering with the received ultrasound signal. The limiter can be used to prevent the transmitted high-voltage electrical excitation from damaging the receive electronics. The limiter and expander can be combined in an expander and limiter element 816, and can also be separate components of the disclosed system. Color flow cross sections of a carotid artery of the mouse were produced at a frame rate of 10,000 frames per second (fps).

Mice were anesthetized with isoflurane (2% in oxygen) and positioned on a mouse imaging stage that provided temperature feedback and heart rate monitoring (THM 100, Indus Instruments, Houston, Tex.). Depilatory cream (Nair™, Carter-Homer, Mississauga, ON, Canada) was used to remove fur from the region of interest. In the case of imaging the mouse heart or carotid artery, the region of interest included the thoracic cage or throat respectively. Ultrasound gel (Aquasonic™ 100, Parker Laboratories, Fairfield, N.J.) was used as coupling fluid between the RMV probe and the skin. Using B-mode imaging on the Vevo660 system, the probe was positioned to provide either a longitudinal section or cross sections of the mouse carotid artery, with the regions of interest located in the focal region of the transducer.

Collected ultrasound data were processed using the Kasai autocorrelation color flow technique as described above. Ensembles of 64 successive demodulated traces from the 10,000 pulses collected at each location were used to produce a series of color flow traces. To maximize the resolution in time, each ensemble was shifted from the previous ensemble by one demodulated trace, leading to an overlay of two successive ensembles of 98.5%. A total of N=9937 ensembles were generated, producing 9937 color flow traces at each transducer location, with a time resolution of 100 µs. To produce a color flow cineloop, color flow traces were then reassembled such that the frame 'number n' ($1 \leq n \leq N$) of the cineloop was composed of the "number n" color flow traces collected at every location. The frame rate of the final cineloop is equal to the PRF (i.e. 10 kHz).

Figure 10:
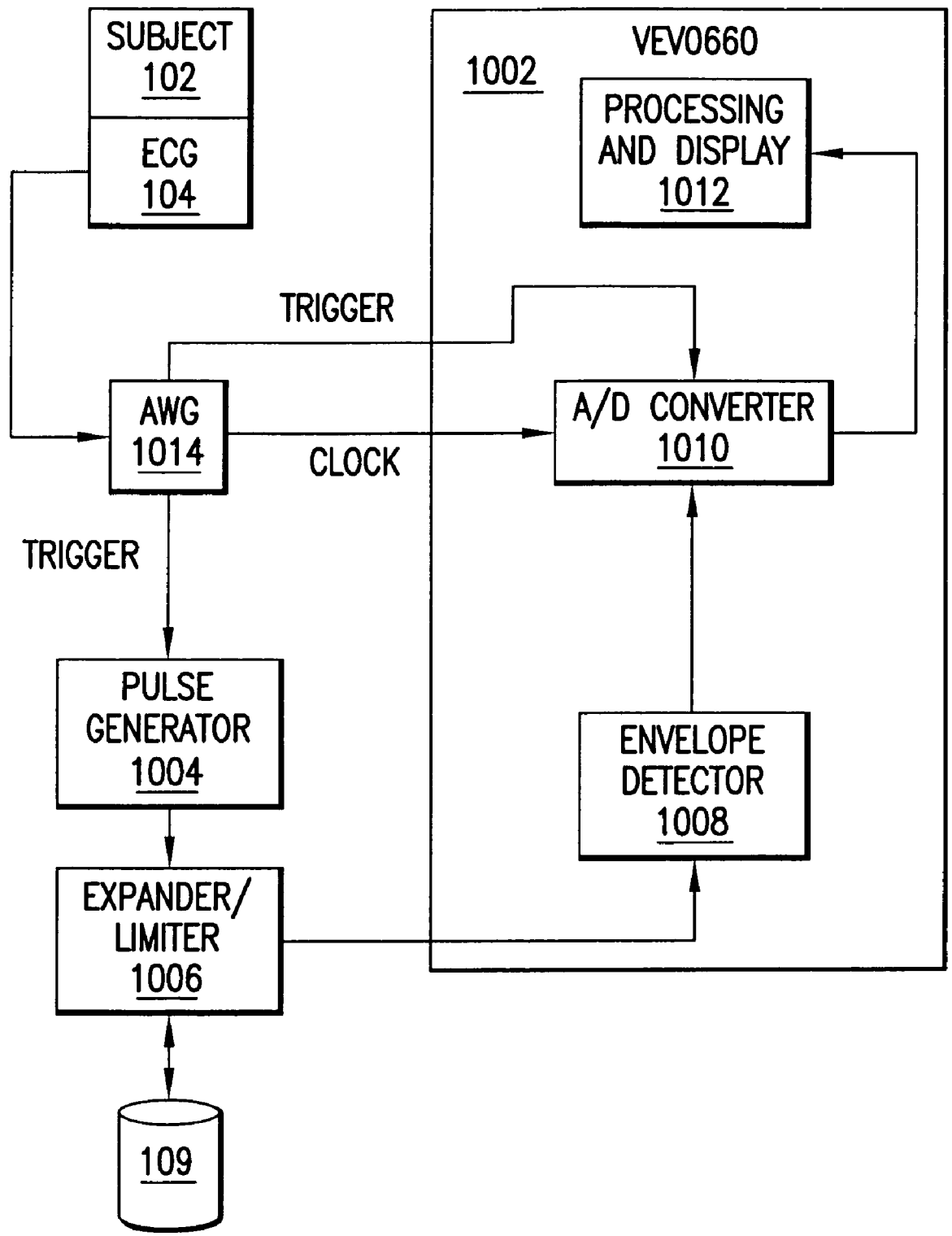
FIG. 10 is a block diagram illustrating an exemplary retrospective B-mode imaging system.

FIG. 10 is a block diagram illustrating an ultrasound system used to produce retrospective B-scan images. As with the ECG-triggered retrospective color flow system, data acquisition for retrospective b-scan imaging was performed using a Vevo660 UBM system 1002 (Visualsonics, Toronto, ON, Canada) For carotid imaging 40 MHz pulse were transmitted by an ultrasound probe 112 comprising an ultrasound transducer 109. For example, a RMV604 probe equipped with a 40 MHz transducer (6 mm focal length) at a PRF of 10 KHz was used. The envelope of the received signals were detected by an envelope detection element 1008 and digitized by an analog to digital converter 1014 by the Vevo660 UBM system. One cycle 30 MHz or 40 MHz pulses were transmitted using a high frequency single cycle pulse generator 1004 (AVB2-C, Avtech Electrosystem, Ogdensburg, N.Y.) triggered by an arbitrary wave form generator 1014 (AWG 2021, Tektronix, Beaverton, Oreg.). The trigger signal comprised a train of 10,000 rectangular pulses separated by 100 µs (PRF=10 kHz). The trigger signal provided by the AWG 1014 was also used to trigger data acquisition by the A/D board 1010, at a sampling clock provided by the AWG 1014. The transducer was kept fixed at successive positions relative to the mouse tissue. At each position, a 10,000 pulse train was transmitted and data were collected before moving the transducer to the next position. Data were acquired at a PRF of 10 KHz, with a step size of 30 µm, over 1.5 mm in a plane perpendicular to the artery, and over 4 mm in a plane parallel to the artery. An expander and limiter element 1006 can also be used. The expander can be used to prevent low amplitude transmitted electronic noise from interfering with the received ultrasound signal. The limiter can be used to prevent the transmitted high-voltage electrical excitation from damaging the receive electronics. The limiter and expander can be combined in an expander and limiter element 1006, and can also be separate components of the disclosed system.

Figure 9:
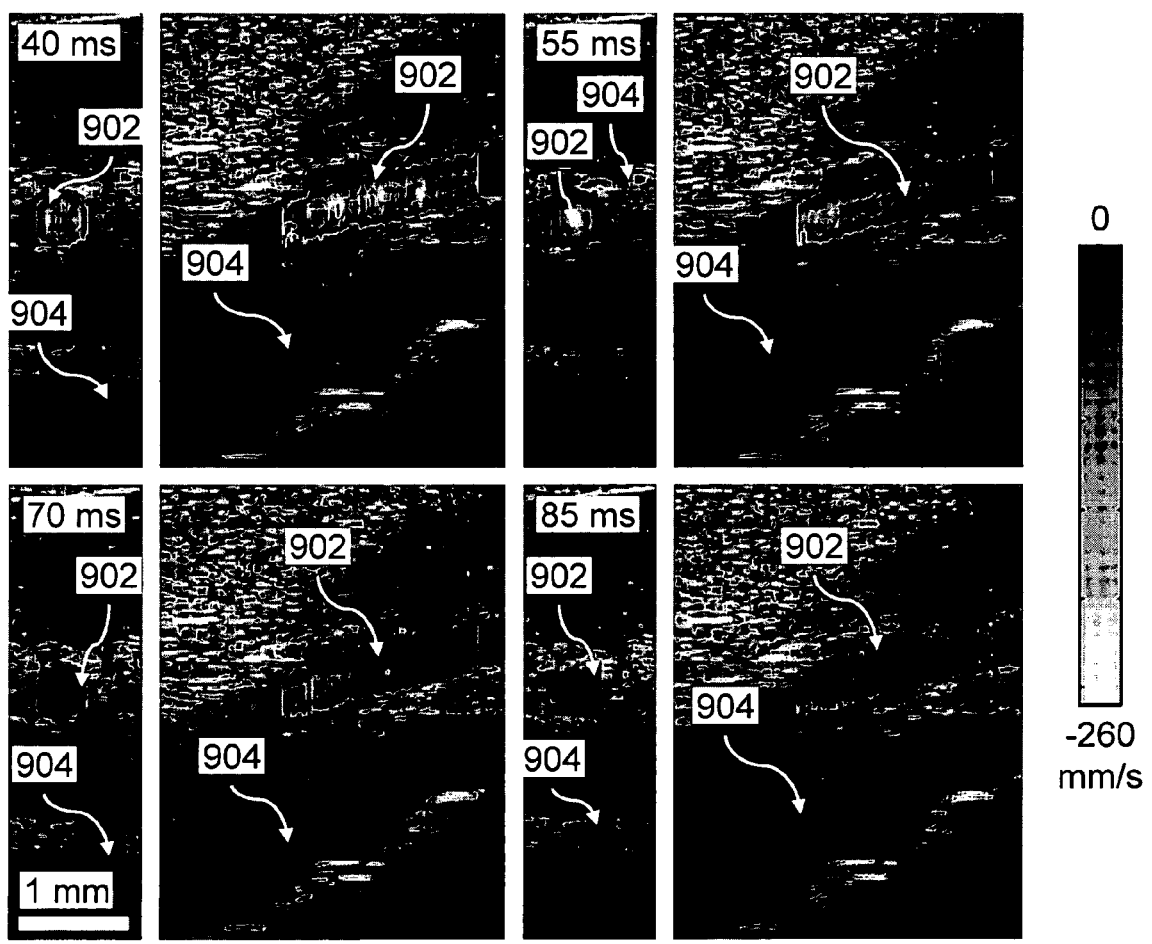
FIG. 9 shows selected reconstructed frames of a mouse carotid artery using the ECG triggered retrospective color flow ultrasound imaging technique.

FIG. 9 shows selected reconstructed frames of the mouse carotid artery using the ECG triggered retrospective color flow ultrasound imaging technique. ECG-triggered retrospective color flow images 902 were overlaid over B-scan images 904 acquired using a retrospective B-mode imaging technique. The detected velocities varied between 10-260 mm/s and were in good agreement with pulsed-wave doppler measurements. The highest detected velocity in the carotid artery was beyond the upper limited of velocity that can be estimated with a PRF of 10 kHz. Clutter filtering was applied to the doppler spectrum.

Assuming that the blood only circulates in one direction in the carotid, negative components of the doppler spectrum in the frequency range from −PRF/2 to 0 were unwrapped (i.e. transferred to the frequency range from PRF/2 to PRF). After zeroing the spectral components from −PRF to 0, the spectrum was transformed back to the time domain and color flow processed using the methods described above.

Only minimal tissue clutter artifacts were observed. These artifacts were only induced by real motion of the tissue, as the transducer was stationary during each acquisition. Spatio-temporal artifacts did not occur because of the inherent properties of the ECG-triggered data acquisition method. An effective frame rate of 10,000 frames/second was achieved, with an estimated optimal acquisition time of 20-30 seconds, corresponding to approximately 100 to 150 heart beats.

Example 2

In Vitro EGC Retrospective Color Flow Imaging Using a Phantom

Both swept-scan color flow imaging and ECG-triggered retrospective color flow imaging were compared using a phantom with a 5-Hz sinusoidally varying velocity profile. The phantom comprises an off-center rotating disk, with an optical sensor which generates an ECG-like pulses on each rotation of the disk.

With a swept-scan technique, good estimation of velocities between 4 mm/s and 35 mm/s were achieved, while with the retrospective technique as described above, good estimation of velocities between 2 mm/s and 35 mm/s were achieved. Spatio-temporal decorrelation artifacts were also examined for each technique. Multiple frames of the swept-scan color flow mapping showed that the locations of velocity components were incoherently positioned between frames, with a frame-rate dependent on the sweep frequency. Multiple frames of the ECG-triggered retrospective color flow mapping, however, showed a gradual velocity change in agreement with the velocity profile of the phantom. Effective frame-rates of 10,000 fps were achieved, compared to 4 fps for the swept-scan method.

The foregoing detailed description has been given for understanding exemplary implementations of the invention only and no unnecessary limitations should be understood there from as modifications will be obvious to those skilled in the art without departing from the scope of the appended claims and their equivalents.

Various publications are referenced in this document. These publications in their entireties are hereby incorporated by reference into this application in order to more fully describe the state of the art to which the disclosed system and method pertains. The references disclosed are also individually and specifically incorporated by reference herein for the material contained in them that is discussed in the sentence in which the reference is relied upon.

What is claimed is:

1. A method of producing an ultrasound image, comprising:
    generating ultrasound;
    transmitting N pulses of the ultrasound into a subject at a first location, wherein a first reference point of an ECG signal taken from the subject triggers the ultrasound transmission;
    receiving N pulses of ultrasound reflected from the subject at the first location;
    transmitting N pulses of the ultrasound into the subject at a second location, wherein a second reference point of an ECG signal taken from the subject triggers the ultrasound transmission;
    receiving N pulses of ultrasound reflected from the subject at the second location;
    processing the N pulses of received ultrasound from the first location to form N' first ultrasound color traces and processing the N pulses of received ultrasound from the second location to form N' second ultrasound color traces, wherein N' is less than or equal to N−1;
    incrementally repeating from n=1 to N' reconstructing the N' first ultrasound color traces and N' second ultrasound color traces into N' image frames, wherein each image frame is comprised of a first line corresponding to the nth first ultrasound color trace and a second line corresponding to the nth second ultrasound trace.

2. The method of claim 1, further comprising generating ultrasound in a frequency of about 20 MHz to 60 MHz.

3. The method of claim 1, further comprising using the ultrasound on a small animal to image blood flow.

4. The method of claim 3, wherein the small animal is a mouse.

5. The method of claim 1, further comprising using the ultrasound on a small animal to produce a blood velocity estimate.

6. The method of claim 5, wherein the small animal is a mouse.

7. The method of claim 1, further comprising overlaying the ultrasound image on a retrospective B-scan ultrasound image.

8. The method of claim 1, wherein the ultrasound is generated by a single element mechanically scanned transducer.

9. The method of claim 1, wherein the ultrasound is generated by an electronically steerable array transducer.

10. The method of claim 1, further comprising displaying a plurality of image frames in series to form a cineloop.

11. A system for developing an ultrasound image, comprising:
    an ultrasound probe having a transducer capable of transmitting and receiving ultrasound energy;
    a transmit subsystem configured to transmit a plurality of ultrasound pulses at a plurality of locations on a subject's anatomy, the plurality of ultrasound pulses transmitted at each of the plurality of locations when triggered by a reference point of an ECG signal;
    a memory on which resides software, wherein received ultrasound energy is input into the software from each of the plurality of locations on a subject's anatomy and corresponding color flow traces are output by the software; and
    a processor configured to generate a plurality of ECG-triggered retrospective color flow ultrasound image frames, wherein each frame is comprised of lines and each line corresponds to one of the color flow traces from one of the plurality of locations on the subject's anatomy, wherein the memory is coupled to the processor.

12. The system of claim 11, wherein the ultrasound occurs at a frequency range of about 20 MHz to 60 MHz.

13. The system of claim 12, wherein the ultrasound is performed on a small animal to image blood flow.

14. The system of claim 13, wherein the small animal is a mouse.

15. The system of claim 11, further comprising:
    a second software residing on the memory, wherein the color flow traces are processed by the second software forming a representation of blood flow over a region or portion of the subject's anatomy.

* * * * *